United States Patent [19]
Bryce et al.

[11] Patent Number: 5,807,900
[45] Date of Patent: Sep. 15, 1998

[54] METHOD FOR IDENTIFYING COMPOUNDS HAVING INCREASED ACTIVITY FOR THE REPAIR OF SKIN PHOTODAMAGE

[75] Inventors: Graeme Findlay Bryce, Upper Montclair; Stanley Seymour Shapiro, Livingston, both of N.J.

[73] Assignee: Hoffmann-La Roche, Inc., Nutley, N.J.

[21] Appl. No.: 414,242

[22] Filed: Mar. 31, 1995

[51] Int. Cl.$^6$ .......................... A61K 31/07; A61K 31/19; A61K 31/38
[52] U.S. Cl. .......................... 514/725; 514/432; 514/557; 514/563; 514/569
[58] Field of Search .................................... 514/432, 557, 514/725, 563, 569

[56] References Cited

U.S. PATENT DOCUMENTS

| | | | |
|---|---|---|---|
| 4,230,701 | 10/1980 | Holick et al. | 424/236 |
| 4,335,120 | 6/1982 | Holick et al. | 424/236 |
| 5,075,333 | 12/1991 | Bryce et al. | 514/481 |
| 5,391,766 | 2/1995 | Klaus et al. | 549/23 |

FOREIGN PATENT DOCUMENTS

| | | |
|---|---|---|
| 552 624 A1 | 7/1993 | European Pat. Off. . |
| WO 88/07857 | 10/1988 | WIPO . |
| WO 93/03713 | 3/1993 | WIPO . |

OTHER PUBLICATIONS

Lehmann et al. Cancer Research 51:4804–4809 (Sep. 15, 1991).

Delescluse et al., Molecular Pharmacology 40(4):556–562 (Oct. 1991).

Graupner et al., Biochem. and Biophys. Res. Comm., 179(3):1554–156 (1991).

Weiss, et al, Topical Tretinoin Improves Photodamage Skin, Jama, vol. 259, No. 4 pp. 527–532 (1988).

Kligman, et al, Topical Retinoic Acid Enhances The Repair Of Ultraviolet Damaged Dermal Connective Tissue, Connective Tissue Research, vol. 12 pp. 139–150 (1984).

Weinstein, et al, Topical Tretinoin for Treatment of Photodamage Skin, Arch Dermatol, vol. 127, pp. 659–665 (1991).

Armstrong, et al, Clinical Panel Assessment Of Photodamage Skin Treated With Isotretinoin Using Photographs, Arch Dermatol, vol. 128, pp. 352–356 (1992).

Apfel, et al, A Retinoic Acid receptor α antagonist selectively counteracts retinoic acid effects, Proc. Natl. Acad. Sci. vol. 89, pp. 7129–7133 (1992).

Bernard, et al, Identification Of Synthetic Retinoids With Selectivity For Human Nuclear Retinoic Acit Receptor γ, Biochemical and Biophysical Research Communications, vol. 186, No. 2, pp. 977–983 (1992).

K. Eckhardt et al., Toxicology Letters, 70:299–308 (1994).

*Primary Examiner*—Phyllis G. Spivack

[57] ABSTRACT

A method of inducing the repair of photodamage to human skin comprising topically administering a composition containing a multi-selective retinoid which transactivates both of the human RAR-α and RAR-γ receptors in combination with a compound which inhibits the binding of said multi-selective compound to the human RAR-α receptor is disclosed.

15 Claims, 3 Drawing Sheets

METHOD FOR IDENTIFYING COMPOUNDS HAVING INCREASED ACTIVITY FOR THE REPAIR OF SKIN PHOTODAMAGE

BACKGROUND OF THE INVENTION

The classical treatments of aged or photoaged skin have generally focused on altering the clinical appearance while not addressing the underlying causes. Thus chemical peels, dermabrasion, collagen injections and surgery were the methods of choice. However, many anecdotal reports on the beneficial effects on skin emerged from the use of all-trans retinoic acid in the treatment of acne. Recent double-blind, vehicle-controlled studies have confirmed these observations and both clinical and histological improvements have been validated (Weiss et al., "Topical tretinoin improves photoaged skin", *J. Amer. Med. Assoc.*, 259:527–532 (1988); Weinstein et al., "Topical tretinoin for the treatment of photodamaged skin: a multicenter study", *Arch Dermatol.*, 127: 659–665 (1991)). In addition, the efficacy of isotretinoin in photodamage has been demonstrated by the use of photographic assessment (Armstrong et al., "Clinical panel assessment of photodamaged skin treated with isotretinoin using photographs", *Arch Dermatol.*, 128: 352–356 (1992)).

Retinoid-induced photodamage repair in the hairless mouse model was first described by Kligman et al. in 1984 (Kligman et al., "Topical retinoic acid enhances the repair of ultraviolet damaged dermal connective tissue", *Conn Tiss Res*, 12:139–150 (1984)). In this publication a description is given of the repair zone, namely the area between the epidermis and the band of compressed elastin in the lower dermis. The authors measured the width of this zone at several points along a histological section and computed an average value. Statements were made to the effect that the width was variable and, in fact zero at some points. The term "focal" has been used to describe this intermittent nature of the repair zone. The focal nature of retinoid-induced repair zones has been a consistent feature reported in the prior art with no obvious explanation.

SUMMARY OF THE INVENTION

The invention permits the identification of compounds which have the ability to induce substantially continuous repair of photodamage in human skin, wherein the zone of photodamage repair induced by the compounds so identified lacks the focal nature of repair zones that were obtained with prior art compounds. The method comprises the steps of 1) measuring the transactivation activity of compounds for each of the human RAR-α and RAR-γ receptors, and 2) selecting compounds which selectively transactivate RAR-γ.

The invention also comprises a method of inducing the repair of photodamage to human skin comprising topically administering a composition containing a multi-selective retinoid which transactivates both of the human RAR-α and RAR-γ receptors in combination with a compound which inhibits the binding of said multi-selective retinoid to the human RAR-α receptor.

DETAILED DESCRIPTION OF THE INVENTION

Figure 1A:
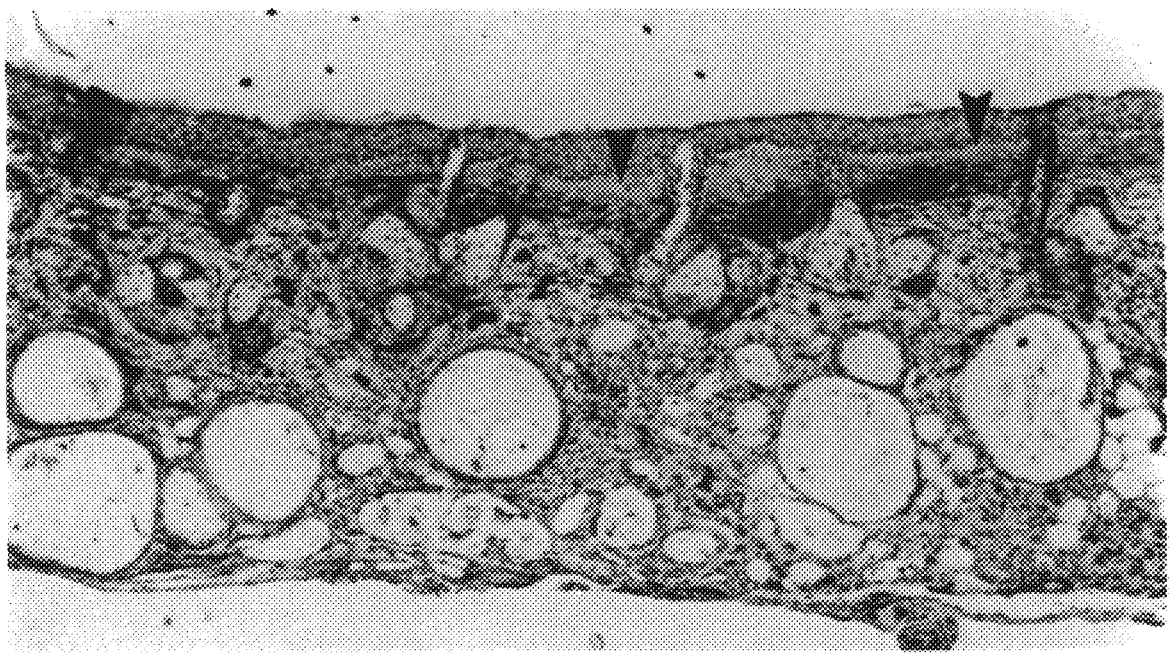
FIG. 1: Skin photodamage repair in the hairless mouse model. Results for a non-γ-selective retinoid (A) and a γ-selective retinoid (B-higher magnification; C-lower magnification).

As used herein a "retinoid" is any compound that is capable of transactivating any or all of the alpha, beta and gamma retinoic acid receptors (RAR-α, RAR-β, and RAR-γ) with an $ED_{50}$ of 1000 nM or less when determined by methods known in the art.

"$ED_{50}$" is the molar concentration of the retinoid which transactivates the particular retinoic acid receptor under consideration by 50% of the maximum transactivation which can be obtained with said retinoid.

"Transactivation" is the ability of a retinoid to activate the transcription of a gene where the gene transcription is initiated by the binding of a ligand to the particular retinoic acid receptor being tested, i.e., RAR-α or RAR-γ in the present case. Determining the ability of a compound to transactivate the RAR-α or RAR-γ receptors may be performed by methods known in the art. Examples of such methods are found in Bernard et al., *Biochem. and Biophys. Res Comm.*, 186:977–983 (Jul. 31, 1992) and Apfel et al., *Proc. Natl. Acad. Sci. USA*, 89:7129–7133 (August 1992). Transactivation assays generally involve the co-transfection of a cell line with an expression vector which causes the expression of the particular retinoic acid receptor and with a reporter gene which is controlled by the receptor. The reporter gene directs the expression of a product which is readily detectable. When a ligand having the ability to transactivate the particular receptor binds to the receptor, the product of the reporter gene is expressed and detected.

In accordance with the invention, it has been discovered that retinoids which have a greater ability to transactivate the RAR-γ receptor in comparison to their ability to transactivate the RAR-α receptor induce a substantially continuous repair of photodamage in photodamaged skin. Such retinoids thus selectively transactivate the RAR-γ receptor, and will be referred to as γ-selective retinoids. The substantially continuous repair effected by γ-selective retinoids is in contrast to the focal repair zone reported in the prior art for non-γ-selective retinoids. The degree to which a retinoid transactivates the RAR-β receptor has not been found to influence the ability of γ-selective retinoids to induce substantially continuous repair of photodamage, and so may be disregarded in practicing the method of the invention.

Thus, the invention comprises a method of selecting retinoids which have the ability to induce substantially continuous repair of photodamage in human skin, wherein the zone of photodamage repair induced by the compounds so identified lacks the focal nature of repair zones that were obtained with prior art compounds. The method comprises the steps of 1) measuring the transactivation activity of compounds for each of the human RAR-α and RAR-γ receptors, and 2) selecting compounds which are "γ-selective," i.e., which selectively transactivate the RAR-γ receptor.

A retinoid is considered to be γ-selective if it transactivates the RAR-γ receptor with an $ED_{50}$ of 1000 nM or less, and the ratio of its RAR-α transactivation $ED_{50}$ to its RAR-γ transactivation $ED_{50}$ is greater than or equal to 10. Preferably, the compound's ratio of RAR-α transactivation $ED_{50}$ to RAR-γ transactivation $ED_{50}$ is greater than 20. The method of determining the ability of a compound to transactivate the RAR-α and RAR-γ receptors is not critical and may be performed by any conventional means. Preferably, the transactivation $ED_{50}$ of a compound for the RAR-α and RAR-γ receptors is determined in accordance with the procedure of Example 2, herein.

In accordance with the invention, it has also been discovered that compounds which have the ability to transactivate both the human RAR-α and RAR-γ receptors ("multi-selective retinoids") will induce substantially continuous repair of photodamage if topically administered subsequent to or in conjunction with the administration of a compound which inhibits the transactivation of the RAR-α receptor (an "RAR-α antagonist"). A retinoid is considered to be multi-selective for the purpose of the present invention if it transactivates the RAR-γ receptor with an $ED_{50}$ of 1000 nM or less, and the ratio of its RAR-α transactivation $ED_{50}$ to its RAR-γ transactivation $ED_{50}$ is less than 10. The preferred multi-selective retinoids are all-trans retinoic acid and 13-cis retinoic acid, and their pharmaceutically acceptable salts, esters and amides. These multi-selective retinoids may be prepared by means known in the art.

A compound is considered an RAR-α antagonist if its binding $IC_{50}$ for RAR-α is less than or equal to 200 nM and if it has a binding $IC_{50}$ for RAR-γ of greater than 4000 nM. The RAR-α transactivation $ED_{50}$ of RAR-α antagonists is preferably greater than 1000 nM. The binding $IC_{50}$ of a retinoid for RAR-α and RAR-γ may be determined by any conventional means. Preferably, the binding $IC_{50}$ is determined by the method of Example 1.

Thus, the invention also comprises a method of inducing the substantially continuous repair of photodamage to human skin comprising topically administering a composition containing an RAR-α antagonist in combination with a multi-selective retinoid in an amount sufficient to induce said photodamage repair. The transactivation of RAR-α by a multi-selective retinoid may be inhibited by any conventional means. Preferably, the transactivation of RAR-α is inhibited by topically applying to the skin to be treated a composition which contains an RAR-α antagonist that inhibits the binding of the multi-selective retinoid to RAR-α. Any conventional RAR-α antagonist may be used in the method of the invention, such as those disclosed in U.S. Pat. No. 5,391,766 ("'766 patent"), the disclosure of which is hereby incorporated by reference. The preferred RAR-α antagonist is p-[(E)-2-[3',4'-dihydro-4',4'-dimethyl-7'-(heptyloxy)-2'H-1-benzothiopyran-6'-yl]propenyl]benzoic acid 1',1'-dioxide (Compound L, herein; Apfel et al., *Proc. Natl. Acad. Sci. USA*, 89:7129–7133 (August 1992), Table 1: "Ro 41-5253"; '766 patent, Example 2 and claim 12). Compound L may be prepared as described in said '766 patent.

The administration of the RAR-α antagonist may be contemporaneous with the application of the multi-selective retinoid (e.g., both compounds may be in the same topical composition, or two compositions, each containing one of the two active ingredients, are applied substantially contemporaneously, i.e., sequentially one after another or within up to five minutes of each other, in no particular order. Alternatively, the administration of the RAR-α antagonist may precede the application of the multi-selective compound, so long as the administration of the multi-selective compound occurs during the time period that the RAR-α inhibition is in effect.

The ability of a composition of the invention to induce repair of photodamaged skin may be determined by any conventional means. One conventional method of determining the ability of a topical composition to repair photodamaged skin is the hairless mouse model described by Kligman et al., supra. Preferably, the hairless mouse test is performed in accordance with Example 3, herein. In this model, repair is defined by the appearance of a zone of normalized dermis extending from the epidermis down to the layer of compressed elastin. The extent of repair is reflected by the width of this zone. Following the light exposure and treatment as described in Example 3, the average area of the repair zone in all of the 100x microscope fields of a histological section of from 1–1.5 mm in length is measured by image analysis. The average width of the repair zone is then calculated by dividing the area by the length of the histological section that was measured. Using the average repair widths from the results of three different dosages, an approximate $ED_{50}$ (in µg of test compound applied to 10 $cm^2$ of skin area) is calculated from a Width of Repair vs. Dosage plot. For test retinoids which result in a focal repair zone, an activity value from 1 to 3 is then assigned to the test compound based on the activity of standard retinoids, 13-cis retinoic acid or all-trans retinoic acid, having a rating of 2 for an $ED_{50}$ of 10 µg. The scale is as follows: 0: inactive, 1: an $ED_{50}$ of 100 µg, 2: an $ED_{50}$ of 10 µg, and 3: an $ED_{50}$ of 1 µg or less (highly active). However, all of these activity values reflect retinoids which resulted in a focal repair zone.

A special category, with an activity value of 4, is reserved for treated photodamage specimens that exhibit long stretches of continuous repair zones, sometimes extending unbroken along the entire length of the histological section. The width of the repair zone is irrelevant to an activity value of 4. In accordance with the invention, this ability to induce the substantially continuous repair of photodamage has been correlated with γ-selective retinoids. Hence, this type of repair will be referred to as the "γ-effect".

Figure 1B:
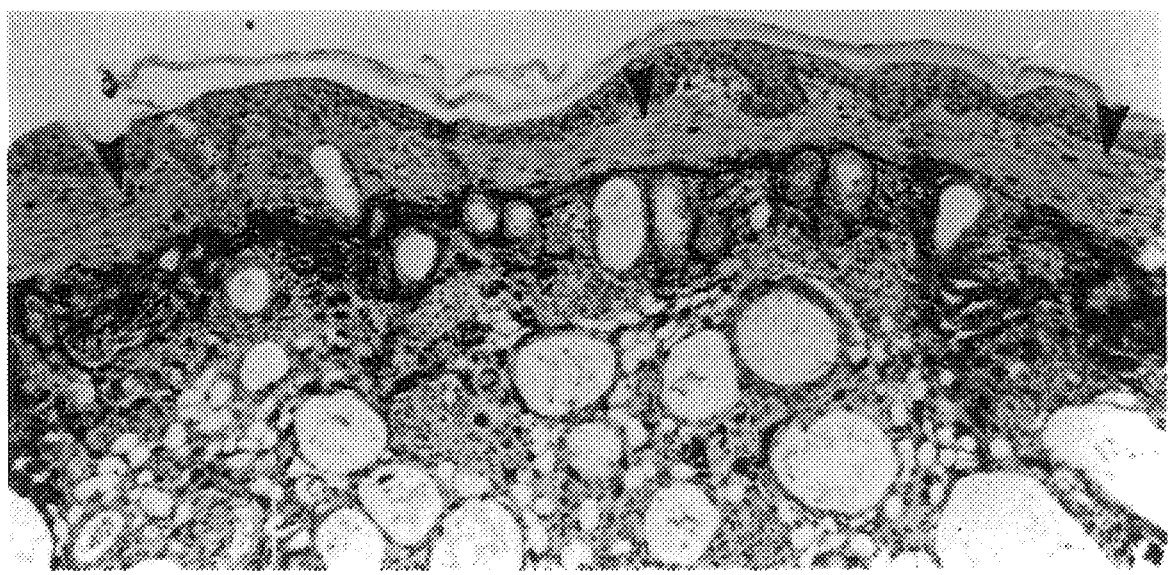
Figure 1C:
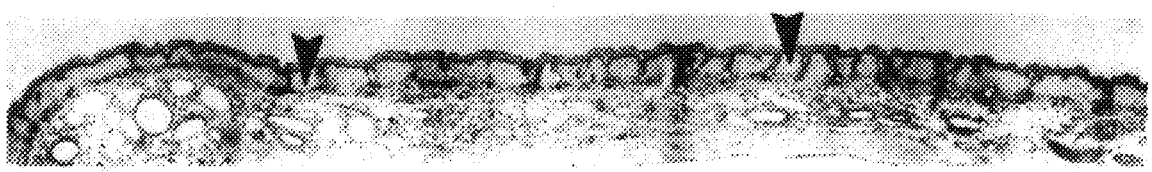

FIG. 1 shows a comparison between the typical results obtained using a non-γ-selective retinoid (A: upper photo) and a γ-selective retinoid selected in accordance with the present invention (B: lower photo) in the hairless mouse model of photodamage. Dermal repair zones are delimited by the the dermal-epidermal junction and the layer of compressed elastin in the lower dermis. In photo A it can be seen that areas of repair, denoted by the arrows, are interspersed with areas with little or no repair. To quantitate the effect, the total area of repair zones in a standard length of tissue is determined by image analysis, preferably as described herein. In photo B, the distinguishing feature of the repair is the continuous nature of the repair zone, which in most cases extends across the entire length of the section. Photo B is an example of the γ-effect for which the test compound or composition would receive an activity value of 4.

The method of the invention whereby skin photodamage is treated by topically applying to the skin in need of such treatment an effective amount of an RAR-α antagonist and a multi-selective retinoid is preferably carried out by topically applying a single composition of the invention containing both the RAR-α antagonist and the multi-selective retinoid admixed with a pharmaceutically acceptable topical carrier. Such topical compositions are described below. However, it is within the scope of the invention to treat photodamage by separately applying two compositions, one of which contains a multi-selective retinoid admixed with a pharmaceutically acceptable topical carrier and the other composition contains the RAR-α antagonist admixed with a pharmaceutically acceptable topical carrier. The two compositions may be applied substantially contemporaneously, i.e., sequentially one after the other or within up to five minutes of each other, in no particular order. Alternatively, the RAR-α antagonist may be applied to the skin so that it is absorbed and has already acted to inhibit RAR-α transactivation when the composition containing the multi-selective retinoid is applied to the skin at a subsequent time. The composition containing the multi-selective retinoid should be applied during the duration that the RAR-α antagonist inhibits RAR-α transactivation. The effective duration of RAR-α transactivation inhibition may be routinely determined by means known in the art.

The topical compositions of the invention containing a multi-selective compound and an RAR-α antagonist are another aspect of the present invention. These compositions should contain from about 0.001 percent to about 0.1 percent by weight of the multi-selective retinoid, and contain from about 0.01 percent to about 1.0 percent by weight of the RAR-α antagonist, but should contain at least 10-fold more of the antagonist, by weight, than of the multi-selective retinoid. Separate compositions containing either the RAR-α antagonist or the multi-selective retinoid preferably contain similar amounts of the respective active ingredients.

It is preferred to practice the method of the invention, whereby the RAR-α antagonist and multi-selective retinoid are applied to the skin for the repair of photodamage, once or twice daily for a period of preferably at least five months. Any conventional method may be used to apply the RAR-α antagonist and multi-selective retinoid to the skin. Any of the means conventional for applying pharmaceuticals in topical compositions which comprise the active ingredient (s) and conventional pharmaceutically acceptable carrriers can be utilized in accordance with the invention.

The pharmaceutical compositions of the invention for topical administration to the skin can be prepared by mixing the aforementioned RAR-α antagonist and/or multi-selective retinoid with non-toxic, therapeutically inert, solid or liquid carriers customarily used in such compositions. The topical compositions of the invention may be formulated using any conventional ingredients known in the art for the preparation of pharmaceutically acceptable carriers. For topical administration to the skin, the compositions of the invention are preferably prepared as ointments, tinctures, creams, gels, solutions, lotions, sprays, suspensions, and the like. In fact, any conventional composition utilized for application to the skin can be utilized in accordance with this invention. Among the preferred methods of applying the composition containing the active ingredient of the invention is to apply the active ingredient of the invention in a pharmaceutically acceptable carrier which is in the form of a gel, lotion or cream.

In preparing the topical compositions described above, additives such as preservatives, thickeners, perfumes and the like conventional in the art of pharmaceutical compounding of topical preparations can be used. In addition, conventional antioxidants may be incorporated into the topical compositions containing the aforementioned multi-selective compound and the RAR-α antagonist. Among the conventional antioxidants which can be utilized in these preparations are included N-methyl-α-tocopherolamine, tocopherols, butylated hydroxyanisole, butylated hydroxytoluene, ethoxyquin and the like. Furthermore, if desired, conventional emulsifying agents can be utilized in the topical preparations of this invention.

Ointment formulations containing the multi-selective compound and the RAR-α antagonist may comprise admixtures of a semi-solid petroleum hydrocarbon with a solvent dispersion of the active ingredient of the invention.

Cream compositions containing the multi-selective compound and the RAR-α antagonist preferably comprise emulsions formed from a water phase of a humectant, a viscosity stabilizer and water, an oil phase of a fatty acid alcohol, a semi-solid petroleum hydrocarbon and an emulsifying agent and a phase containing the active ingredient of the invention dispersed in an aqueous stabilizer-buffer solution. Stabilizers may be added to the topical composition. Any conventional stabilizer can be utilized in accordance with this invention. In the oil phase, fatty acid alcohol components function as a stabilizer. These fatty acid alcohol components are preferably derived from the reduction of a long-chain saturated fatty acid of at least about 14 carbon atoms. Cream-base pharmaceutical formulations containing the active ingredient of the invention may be composed of, for example, aqueous emulsions containing a fatty acid alcohol, semi-solid petroleum hydrocarbon, 1,2-ethyleneglycol and an emulsifying agent.

In accordance with the invention, the following compounds were evaluated for their RAR binding and transactivation properties, and for their ability to repair photodamage in the hairless mouse model:

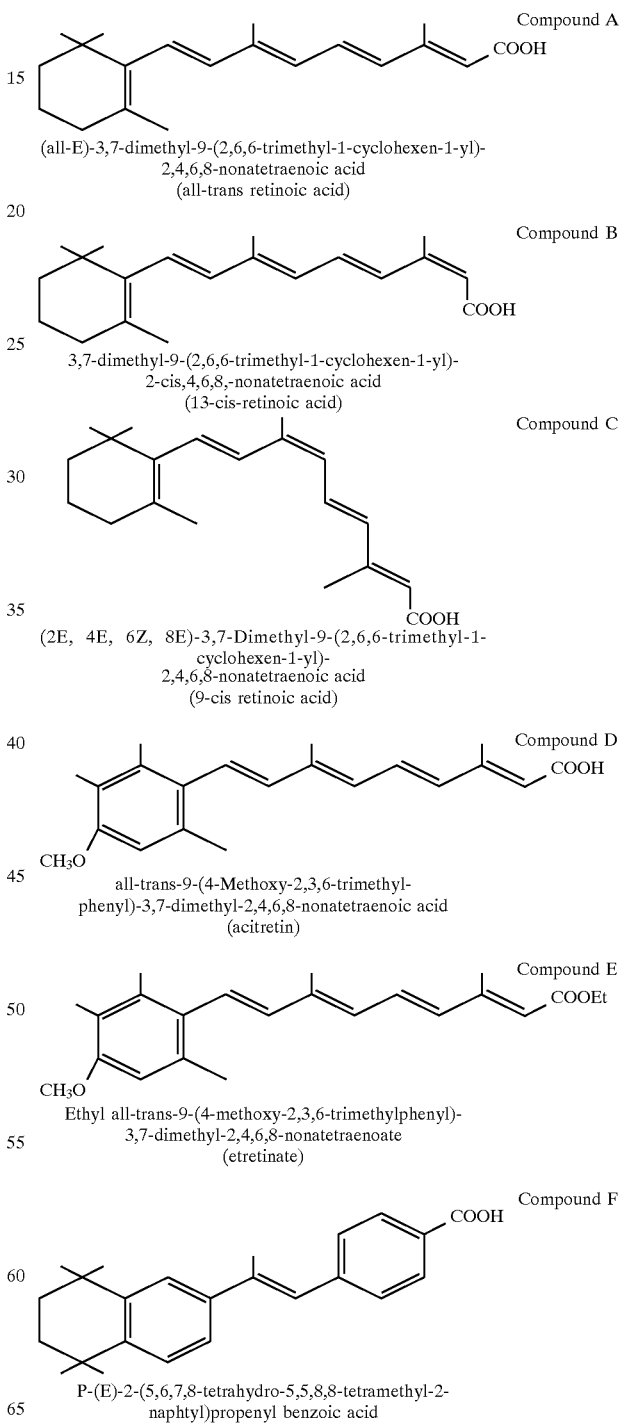

Compound A
(all-E)-3,7-dimethyl-9-(2,6,6-trimethyl-1-cyclohexen-1-yl)-2,4,6,8-nonatetraenoic acid
(all-trans retinoic acid)

Compound B
3,7-dimethyl-9-(2,6,6-trimethyl-1-cyclohexen-1-yl)-2-cis,4,6,8,-nonatetraenoic acid
(13-cis-retinoic acid)

Compound C
(2E, 4E, 6Z, 8E)-3,7-Dimethyl-9-(2,6,6-trimethyl-1-cyclohexen-1-yl)-2,4,6,8-nonatetraenoic acid
(9-cis retinoic acid)

Compound D
all-trans-9-(4-Methoxy-2,3,6-trimethyl-phenyl)-3,7-dimethyl-2,4,6,8-nonatetraenoic acid
(acitretin)

Compound E
Ethyl all-trans-9-(4-methoxy-2,3,6-trimethylphenyl)-3,7-dimethyl-2,4,6,8-nonatetraenoate
(etretinate)

Compound F
P-(E)-2-(5,6,7,8-tetrahydro-5,5,8,8-tetramethyl-2-naphtyl)propenyl benzoic acid

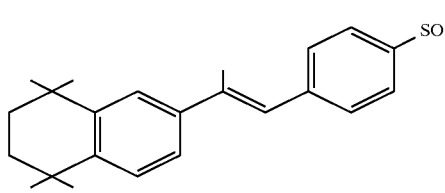

1,2,3,4-tetrahydro-1,1,4,4-tetramethyl-6-
[alpha-methyl-p-(methylsulfonyl)styryl]napthalene Compound G

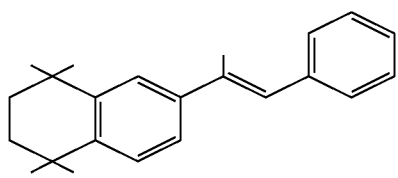

1,2,3,4-tetrahydro-1,1,4,4-tetramethyl-6-
[(E)-alpha-methylstyryl]napthalene

Compound H

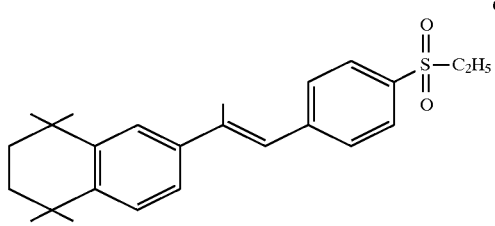

Ethyl p-[(E)-2-(5,6,7,8-tetrahydro-5,5,8,8-tetramethyl-2-
naphthyl)-propenyl]phenyl sulfone Compound I

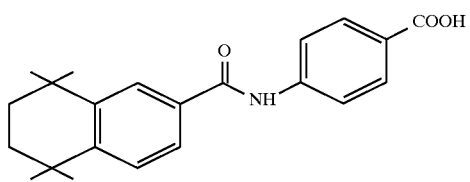

p-(5,6,7,8-tetrahydro-5,5,8,8-tetramethyl-2-
naphthalenecarboxamido)benzoic acid Compound J

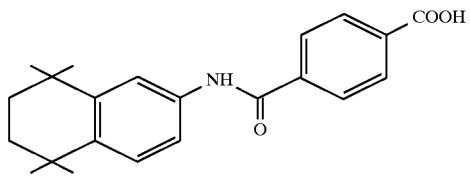

p-[5,6,7,8-tetrahydro-5,5,8,8-tetramethyl-2-naphthyl)
carbamoyl]benzoic acid

Compound K

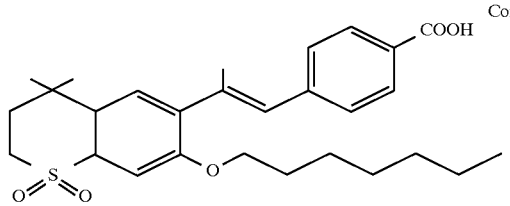

p-[(E)-2-[3',4'-Dihydro-4',4'-dimethyl-7'-(heptyloxy)-2'H-1-
benzothiopyran-6'-yl]propenyl]benzoic acid 1',1'-dioxide Compound L

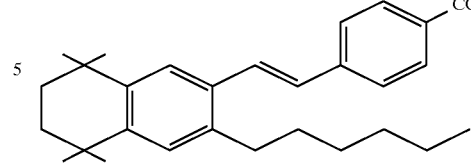

p-[(E)-2-(3-Hexyl-5,6,7,8-tetrahydro-5,5,-
8,8-tetramethyl-2-naphthyl)vinyl]benzoic acid Compound M

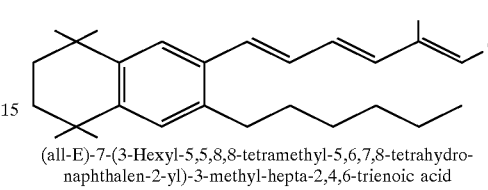

(all-E)-7-(3-Hexyl-5,5,8,8-tetramethyl-5,6,7,8-tetrahydro-
naphthalen-2-yl)-3-methyl-hepta-2,4,6-trienoic acid Compound N

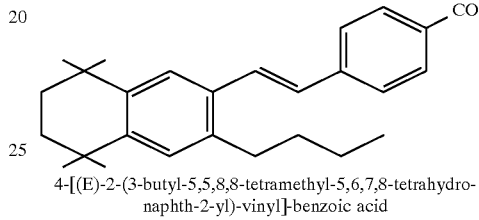

4-[(E)-2-(3-butyl-5,5,8,8-tetramethyl-5,6,7,8-tetrahydro-
naphth-2-yl)-vinyl]-benzoic acid Compound O

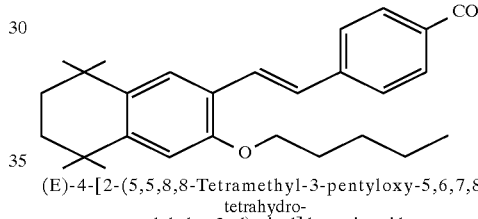

(E)-4-[2-(5,5,8,8-Tetramethyl-3-pentyloxy-5,6,7,8-
tetrahydro-
naphthalen-2-yl)-vinyl]-benzoic acid Compound P

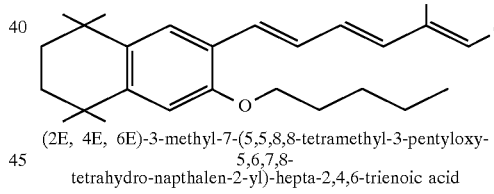

(2E, 4E, 6E)-3-methyl-7-(5,5,8,8-tetramethyl-3-pentyloxy-
5,6,7,8-
tetrahydro-napthalen-2-yl)-hepta-2,4,6-trienoic acid Compound Q

EXAMPLE 1

Binding Assay for Human RAR-α, RAR-β and RAR-γ

Binding assays were performed essentially as described in Apfel et al., supra. The putative ligand binding domains of RAR-α, RAR-β, and RAR-γ (DEF-domain, 262, 255 and 296 amino acids, respectively) were expressed in *E.coli*. Extracts containing the receptors were used in a competitive binding assay which depends upon the ability of increasing concentrations of a retinoid to displace $^3$H-retinoic acid. In a typical assay, 0.2 to 0.4 picomoles of receptors were incubated in 0.2 ml of 50 mM Tris HCl, pH 7.4, 50 mM NaCl, 2 mM EDTA (binding buffer) containing 0.5% gelatin, 1% DMSO, 2–5 nM $^3$H-retinoic acid and various concentrations of unlabelled retinoids. After 3–5 hours at 22° C., 0.15 ml of chilled charcoal/dextran suspension (5% Norit A/0.5% dextran T-40 in binding buffer) were added for 15 min at 4° C. The tubes were centrifuged at 12,000 x g for 15 minutes and the supernates counted. Binding parameters were calculated from competition curves using the Ligand program. Nonspecific binding measured in the presence of 1 $\mu$M unlabelled retinoic acid was 5–10% of the total added counts.

Data are means of values obtained from two or more individual experiments, rounded off to two significant figures. $IC_{50}$=retinoid concentration at which labelled retinoic acid binding is inhibited by 50%. When binding inhibition at 10,000 nM is less than 50%, >10,000 is indicated. Results are shown in Table 1.

EXAMPLE 2

Retinoid Receptor Transactivation Assays

Transactivation assays were performed essentially as described in Apfel et al., supra. For the RAR transcription activation test system, the secreted alkaline phosphatase gene (SeAP) is used as reporter. To have a screening system specific for the transfected receptor, chimeric receptors are used. These contain an estrogen receptor DNA binding domain and therefore recognize the estrogen response element (ERE) which no endogenous RAR's in mammalian cells will recognize.

The transactivation assay system has been adapted to 96-well plates and most steps are done by a robot. Briefly, on day 1 confluent COS cells are subcultured at an equivalent density onto 96-well plates in DMEM+10% charcoal stripped serum. On day 2 DNA is prepared for transfection by mixing the following: 10 $\mu$g vit-TK-SeAP reporter plasmid, 2 $\mu$g RAR expression plasmid, 2 $\mu$g transfection control plasmid and 30 $\mu$l Transfectam (lipopolyamine transfection reagent). Cells are washed twice with serum-free medium and DNA/transfectam mix added. After 1 hour medium is removed and replaced with growth medium containing test retinoids. On day 4 or 5 the culture supernatant is removed, heated to 65° for 5 min to inactivate nonspecific phosphatases, and diluted 1:10 with water. 20 $\mu$l samples are added to 100 $\mu$l of phosphatase substrate in buffer. After 1 hour at 37° the luminescence is measured in a 96-well luminometer.

100 $\mu$l of $\beta$-galactosidase substrate is added to the adherent cells. Plates are incubated for 1 hour at 37° and the supernatants transferred to separate plates for quantitation of $\beta$-galactosidase activity by luminescence measurement. Transactivation results are expressed as the ratio of SeAP/$\beta$-galactosidase activity for each well to correct for well-to-well variation in transfection efficiency.

Data are means of values obtained from two or more individual experiments, rounded off to two significant figures. To determine the molar concentration which corresponds to 50% of the maximum transactivation activity of the test compound ($ED_{50}$), the transactivation activity of the test retinoids is determined at several concentrations, and an Activity vs. Concentration plot is made. The maximum transactivation activity is determined from the plot where increasing dosage provides little or no additional activity, i.e., where the plot begins to level off. For active retinoids the highest concentration tested is 1000 nM. When the transactivation activity of the test retinoid has not reached a maximum at the highest concentration tested, the $ED_{50}$ is arbitrarily considered to be the highest concentration tested (usually 1000 nM). The percent of maximum induction is also determined. % max=(induction level obtained with test retinoid)/(induction level of all-trans-retinoic acid)×100, in the same experiment and with both retinoids at the same concentration (1,000 nM or 10,000 nM, depending on the highest concentration tested). Results are shown in Table 1, with the % max in parentheses..

EXAMPLE 3

Measurement of Photodamage Repair

Hairless mice (female, HRS/J strain, Jackson Labs, 5–7 weeks old at the start of the experiments) were housed in yellow light and irradiated three times per week with a bank of 8 Westinghouse Sunlamps (FS120) placed about 20 cm above the animals. Daily doses were 0.03 J/cm$^2$ for two weeks, 0.06 J/cm2 for two weeks and 0.08 J/cm2 thereafter. The radiation dose is controlled by an International Light Model IL844A Phototherapy Exposure Control and a model SEE240 detector. There is significant elastosis, detectable by histology, after a total dose of about 3.5–4.0 J/cm2 (accumulated over a period of 5–6 months); this can be confirmed by measurements of elastin in whole skin by means of a radioimmunoassay for desmosine, an elastin-specific amino acid found in hydrolysates of elastin and considered to be a reliable index of total elastin content.

To effect repair of the dermal damage, the UVB irradiation was discontinued and the animals were divided into groups of approximately eight and treated three times per week with various concentrations of the retinoids dissolved in acetone. Stock solutions are made up freshly every week in subdued light at concentrations such that the dose is delivered in 100 $\mu$l volume and applied topically with a plastic pipette to an area of about 10 cm$^2$ on the back of the animal. All dosing was done under yellow light. A control group treated with acetone alone was included.

Two-cm strips of dorsal skin were taken longitudinally down the center of the irradiated (and treated) area. Elastin fibers were stained with Luna's aldehyde fuchsin and collagen by Van Gieson. In this model, repair is defined by the appearance of a normalized dermis extending from the epidermis down to the layer of compressed elastin. The extent of repair is reflected by the width of this zone. In these studies, since the width of the zone varies considerably, the area of the zone on a standard length of histological section is measured by an image analyzer. Twenty-four fields each of which, at 100X magnification, represents a section of tissue 0.57 mm long, are examined and the area calculated. The results are reported as the average area per field in mm$^2$. Thus the average width of the repair zone can be obtained by dividing this average area by 0.57 mm. Areas of substantial repair are interspersed with areas with no discernible repair. This "focal" nature of the effect is reflected in large standard deviations and increments which sometimes do not reach statistical significance. All microscopic fields are included in the calculations of average area (or width). Data are analyzed by Student's t-test.

Compounds are tested at three doses and an approximate $ED_{50}$ calculated. Based on the activity of standard retinoids, an analog scale has been derived, ranging from 0 (inactive) to 4 (substantially continuous repair. Results are shown in Table 1.

TABLE 1

Activity of Retinoids in Receptor Binding/Transactivation and in Photodamage Repair

| Compound | Activity | Binding IC$_{50}$ | Transactivation ED$_{50}$ (% max) |
|---|---|---|---|
| A (all-trans RA) | 2 | 14 (α) | 6.7 (100) |
|  |  | 14 (β) | 2.8 (100) |
|  |  | 14 (γ) | 3.5 (100) |
| B (13-cis RA) | 2 | 125 | 16 (70) |
|  |  | 100 | 8.5 (64) |
|  |  | 75 | 3.0 (70) |
| C (9-cis RA) | 2 | 260 | 15 (105) |
|  |  | 230 | 14 (108) |
|  |  | 260 | 13 (121) |
| D (acitretin) | 0 | >10000 | 60 (63) |
|  |  | >10000 | 50 (73) |
|  |  | >10000 | 34 (79) |
| E (etretinate) | 0 | >10000 | 1000 (14) |
|  |  | >10000 | 1000 (21) |
|  |  | >10000 | 1000 (20) |
| F | 1 | 36 | 2.1 (106) |
|  |  | 22 | 0.8 (105) |
|  |  | 15 | 3.2 (82) |
| G | 3 | >10000 | 1000 (23) |
|  |  | >10000 | 1000 (17) |
|  |  | >10000 | 1000 (36) |
| H | 0 | >10000 | 1000 (12) |
|  |  | >10000 | 1000 (10) |
|  |  | >10000 | 1000 (19) |
| I | 3 | >10000 | 1000 (10) |
|  |  | >10000 | 1000 (21) |
|  |  | >10000 | 1000 (21) |
| J | 0 | 39 | 3 (95) |
|  |  | 870 | 24 (63) |
|  |  | 4800 | 25 (72) |
| K | 0 | 150 | 3 (83) |
|  |  | 5000 | 48 (96) |
|  |  | >10000 | 48 (109) |
| L | 0 | 70 | 1000 (14) |
|  |  | 4700 | 1000 (14) |
|  |  | 4200 | 1000 (18) |
| M | 4 | 2200 | 1000 (24) |
|  |  | 2300 | 88 (62) |
|  |  | 210 | 15 (36) |
| N | 4 | 1500 | 1000 (63) |
|  |  | 2900 | 1000 (60) |
|  |  | 170 | 64 (123) |
| O | 4 | 1500 | 130 (56) |
|  |  | 1800 | 30 (88) |
|  |  | 170 | 6 (105) |
| P | 4 | >10000 | 1000 (16) |
|  |  | 7600 | 150 (60) |
|  |  | 670 | 29 (90) |
| Q | 4 | >10000 | 1000 (45) |
|  |  | 9300 | 150 (81) |
|  |  | 2000 | 29 (96) |

Units:
Binding: IC$_{50}$ in nM
Transactivation: ED$_{50}$ in nM, % max in parentheses

EXAMPLE 4

Photodamage repair obtained from the combination of RARα-antagonist and a multi-selective compound Compound A (all-trans retinoic acid) was evaluated for photodamage repair in the hairless mouse model as described in Example 3, both alone and in combination with Compound L, which is an RARα-antagonist. Compound A, alone, had an activity of 2. The RAR-α antagonist by itself had an activity of 0 (inactive). However, the combination of 20 μg of Compound A and 200μg of Compound L (administered to 10 cm² of the mouse skin as described in Example 3) gave substantial levels of repair, including showing the pattern of long stretches of continuous repair (activity=4) which was previously only seen from γ-selective compounds.

EXAMPLE 5

Exemplary topical compositions

A. Lotion

|  |  | preferred |
|---|---|---|
| Multi-selective retinoid | 0.001–0.1 g |  |
| RAR-α antagonist | 0.01–1.0 g* |  |
| Propylene Glycol | 5.00–20.00 g | 10.00 g |
| PEG-Glyceryl Cocoate** | 0.00–20.00 g | 10.00 g |
| dl-a-tocopherol | 0.001–0.50 g | 0.02 g |
| Ascorbyl Palmitate | 0.01–0.20 g | 0.10 g |
| Propyl Gallate | 0.001–0.02 g | 0.002 g |
| Citric acid, anhydr.*** | 0.00–0.20 g | 0.01 g |
| Isopropanol**** | 40.00–90.00 g | 50.00 g |
| Water, dem. ad | 100.00 g | 100.00 g (resp. ml) |

*at least 10-fold the amount of the multi-selective retinoid
**or other tensides
***or other complexing agents,. e.g., ETDA
****or other alcohols, e.g., ethanol B. Gel

|  |  | preferred |
|---|---|---|
| Multi-selective retinoid | 0.001–0.1 g |  |
| RAR-α antagonist | 0.01–1.0 g* |  |
| Propylene Glycol | 5.00–20.00 g | 10.00 g |
| PEG-Glyceryl Cocoate** | 0.00–20.00 g | 10.00 g |
| dl-a-tocopherol | 0.001–0.50 g | 0.02 g |
| Ascorbyl Palmitate | 0.01–0.20 g | 0.10 g |
| Propyl Gallate | 0.001–0.02 g | 0.002 g |
| Citric acid, anhydr.*** | 0.00–0.20 g | 0.01 g |
| Isopropanol**** | 40.00–90.00 g | 50.00 g |
| HPMC***** | 0.50–5.00 g | 3.00 g |
| Water, dem. ad | 100.00 g | 100.00 g |

*at least 10-fold the amount of the multi-selective retinoid
**or other tensides
***or other complexing agents as EDTA
****or other alcohols e.g. Ethanol
*****Hydroxypropyl Methylcellulose or other polymer e.g. neutralized Carbomer, Methyl Cellulose, Sodium Carboxymethycellulose
******Preservatives, e.g. Parben esters (methyl, ethyl, propyl, butyl), Sorbic Acid Benzoic Acid C. Cream

|  |  | preferred |
|---|---|---|
| Multi-selective retinoid | 0.001–0.1 g |  |
| RAR-α antagonist | 0.01–1.0 g* |  |
| Glycerol | 0.00–10.00 g | 5.00 g |
| Na$_2$ETDA | 0.001–0.50 g | 0.03 g |
| Glycerides** | 5.00–20.00 g | 10.00 g |
| Cetyl Acohol | 0.50–5.00 g | 1.00 g |
| Stearyl Alcohol | 0.50–5.00 g | 1.00 g |
| Glycerol mono Stearate | 1.00–8.00 g | 4.00 g |
| Cetaereth | 0.50–5.00 g | 2.00 g |
| dl-α-Tocopherol | 0.001–0.50 g | 0.02 g |
| Preservatives**** | q.s. | q.s. |
| Water, dem. ad | 100.00 g | 100.00 g |

*at least 10-fold the amount of the multi-selective retinoid
**e.g. caprylic/capric triglyceride, caprylic/capric/linoleic triglyceride, natural glycerides, as well as, e.g., propylene glycol, dicaprylate/dicaprate and waxes such as stearyl stearate, oleyl oleate, and isopropyl myristate
***Cetaereth 5-30, or other emulsifiers such as Polysorbate 20-80, Sorbitane esters of fatty acids, and fatty acid esters of PEG
****Preservatives, e.g., parben esters (methyl, ethyl, propyl, butyl), sorbic acid, benzoic acid

We claim:
1. A method of treating photodamage in human skin in need of such treatment comprising topically administering to said skin to induce substantially continuous repair of said photodamage a composition comprising:
   a) 0.001–0.1 percent by weight of the total composition of a multi-selective retinoid which:
      i) transactivates the RAR-γ receptor by 50% of the maximum transactivation obtained with said retinoid at a concentration of said retinoid of 1000 nM or less, and ii) the ratio of the concentration of said retinoid required to transactivate the human RAR-α receptor at 50% of the maximum RAR-α transactivation obtained with said retinoid to the molar concentration of said retinoid required to transactivate the human RAR-γ receptor at 50% of the maximum RAR-γ transactivation obtained with said retinoid is less than 10;

b) 0.01–1.0 percent by weight of the total composition of an RAR-α antagonist, the amount of said antagonist being at least 10-fold greater by weight than the amount of said multi-selective retinoid, where said antagonist:
  i) inhibits the binding of all-trans retinoic acid to the RAR-α receptor by at least 50% at a concentration of said antagonist of less than or equal to 200 nM,
  ii) inhibits the binding of all-trans retinoic acid to the RAR-γ receptor by 50% at a concentration of said antagonist of no less than 4000 nM; and
  iii) transactivates the RAR-α receptor by 50% of the maximum transactivation obtained by said antagonist at a concentration of said antagonist of no less than 1000 nM; and c) the remainder being a pharmaceutically acceptable carrier for topical administration;

wherein said composition is administered in an amount sufficient to induce said photodamage repair.

2. The method of claim 1 wherein the multi-selective compound is all-trans retinoic acid.

3. The method of claim 2 wherein the composition is in the form of a cream, lotion or ointment.

4. The method of claim 3 wherein the composition is applied once or twice daily.

5. The method of claim 1 wherein the multi-selective compound is 13-cis retinoic acid.

6. The method of claim 5 wherein the composition is in the form of a cream, lotion or ointment.

7. The method of claim 6 wherein the composition is applied once or twice daily.

8. A method of treating photodamage in human skin in need of such treatment comprising topically administering to said skin to induce substantially continuous repair of said photodamage:
  a) first composition comprising 0.001–0.1 percent by weight of the total composition of a multi-selective retinoid and the remainder being a pharmaceutically acceptable carrier for topical administration, wherein said multi-selective retinoid:
    i) transactivates the RAR-γ receptor by 50% of the maximum transactivation obtained with said retinoid at a concentration of said retinoid of 1000 nM or less, and
    ii) the ratio of the concentration of said retinoid required to transactivate the human RAR-α receptor at 50% of the maximum RAR-α transactivation obtained with said retinoid to the molar concentration of said retinoid required to transactivate the human RAR-γ receptor at 50% of the maximum RAR-γ transactivation obtained with said retinoid is less than 10;

b) a second composition comprising 0.01–1.0 percent by weight of the total composition of an RAR-α antagonist and the remainder being a pharmaceutically acceptable carrier for topical administration, wherein the amount of said antagonist is at least 10-fold greater by weight than the amount of said multi-selective retinoid and where said antagonist:
    i) inhibits the binding of all-trans retinoic acid to the RAR-α receptor by at least 50% at a concentration of said antagonist of less than or equal to 200 nM,
    ii) inhibits the binding of all-trans retinoic acid to the RAR-γ receptor by 50% at a concentration of said antagonist of no less than 4000 nM; and
    iii) transactivates the RAR-α receptor by 50% of the maximum transactivation obtained by said antagonist at a concentration of said antagonist of no less than 1000 nM;

wherein said first composition and said second composition are administered in an amount sufficient to induce said photodamage repair.

9. The method of claim 8 wherein said first composition and said second composition are applied substantially contemporaneously.

10. The method of claim 9 wherein the multi-selective compound is all-trans retinoic acid.

11. The method of claim 10 wherein said first composition and said second composition are independently in the form of a cream, lotion or ointment.

12. The method of claim 11 wherein said first composition and said second composition are applied once or twice daily.

13. The method of claim 9 wherein the multi-selective compound is 13-cis retinoic acid.

14. The method of claim 13 wherein said first composition and said second composition are independently in the form of a cream, lotion or ointment.

15. The method of claim 14 wherein said first composition and said second composition are applied once or twice daily.

* * * * *